US012551613B2

(12) United States Patent
Hansen et al.

(10) Patent No.: US 12,551,613 B2
(45) Date of Patent: Feb. 17, 2026

(54) IMPLANTABLE DRUG DELIVERY PORT

(71) Applicant: Medtronic, Inc., Minneapolis, MN (US)

(72) Inventors: Lloyd V. Hansen, Hugo, MN (US); Cynthia Nelson Konen, Zimmerman, MN (US); Luis E. Fesser, St. Paul, MN (US); John P. Mehawej, Plymouth, MN (US); Todd Hanson, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 1048 days.

(21) Appl. No.: 17/085,682

(22) Filed: Oct. 30, 2020

(65) Prior Publication Data

US 2022/0133992 A1 May 5, 2022

(51) Int. Cl.
*A61M 5/142* (2006.01)
*A61M 5/165* (2006.01)

(52) U.S. Cl.
CPC ........ *A61M 5/14276* (2013.01); *A61M 5/165* (2013.01); *A61M 2205/02* (2013.01)

(58) Field of Classification Search
CPC .. A61M 5/14276; A61M 5/165; A61M 39/02; A61M 39/0247; A61M 39/04; A61M 2039/0063; A61M 2039/0072; A61M 2039/0081; A61M 2039/009; A61M 2039/0205; A61M 2039/0202; A61M 2039/066; A61M 2039/0261; A61M 2039/0226
See application file for complete search history.

(56) References Cited

U.S. PATENT DOCUMENTS

| | | |
|---|---|---|
| 5,045,064 A | 9/1991 | Idriss |
| 5,085,644 A | 2/1992 | Watson et al. |
| 5,185,003 A | 2/1993 | Brethauer |

(Continued)

FOREIGN PATENT DOCUMENTS

| | | |
|---|---|---|
| CN | 208838708 U | 5/2019 |
| WO | WO0066204 A1 | 11/2000 |

(Continued)

OTHER PUBLICATIONS

EP Search Report corresponding to EP 21205164.3 dated Apr. 7, 2022.

(Continued)

*Primary Examiner* — Michael J Tsai
*Assistant Examiner* — Justin L Zamory
(74) *Attorney, Agent, or Firm* — Draft Masters IP, LLC

(57) ABSTRACT

A drug delivery port including a port housing having an inner sidewall defining a fill port cavity and a fill port washer in direct contact with a perimeter edge of the inner sidewall of the port housing such that an intersection between the washer and the perimeter edge define a plurality of filter channels having a cross-sectional flow area of about 0.001 $mm^2$ to about 0.5 $mm^2$ that lie within the fluid pathway of the delivery port. The delivery port also includes a port cover coupled and a pierceable septum compressed between the fill port washer and the port cover configured to allow a needle to pierce through the septum to deliver an injectable fluid to the fill port cavity.

4 Claims, 6 Drawing Sheets

(56) References Cited

U.S. PATENT DOCUMENTS

| | | | | |
|---|---|---|---|---|
| 5,281,210 | A | 1/1994 | Burke et al. | |
| 5,527,307 | A | 6/1996 | Srisathapat et al. | |
| 5,575,770 | A * | 11/1996 | Melsky | A61M 5/14276 604/86 |
| 5,695,490 | A * | 12/1997 | Flaherty | A61M 39/0208 604/288.02 |
| 5,702,372 | A | 12/1997 | Nelson | |
| 5,833,654 | A | 11/1998 | Powers et al. | |
| 5,957,890 | A | 9/1999 | Mann et al. | |
| 6,013,051 | A | 1/2000 | Nelson | |
| 6,042,579 | A | 3/2000 | Elsberry et al. | |
| 6,572,583 | B1 | 6/2003 | Olsen et al. | |
| 6,852,106 | B2 | 2/2005 | Watson et al. | |
| 6,962,577 | B2 | 11/2005 | Tallarida et al. | |
| 7,351,239 | B2 | 4/2008 | Gill | |
| 7,366,562 | B2 | 4/2008 | Dukesherer et al. | |
| 7,637,897 | B2 | 12/2009 | Ginggen | |
| 7,803,143 | B2 | 9/2010 | Tallarida et al. | |
| 7,963,956 | B2 | 6/2011 | Kunst | |
| 8,320,991 | B2 | 11/2012 | Jascob et al. | |
| 8,419,710 | B2 | 4/2013 | Keimel et al. | |
| 8,483,802 | B2 | 7/2013 | Kalpin et al. | |
| 8,545,484 | B2 | 10/2013 | Haase et al. | |
| 8,591,456 | B2 | 11/2013 | Steinbach | |
| 8,613,724 | B2 | 12/2013 | Lanier, Jr. et al. | |
| 8,721,605 | B2 | 5/2014 | Brandt et al. | |
| 8,915,893 | B2 | 12/2014 | Steinbach | |
| 8,932,271 | B2 | 1/2015 | Hamatake et al. | |
| 9,079,004 | B2 | 7/2015 | Wiley et al. | |
| 9,427,553 | B2 | 8/2016 | Nelson | |
| 9,433,764 | B2 | 9/2016 | East et al. | |
| 9,744,338 | B2 | 8/2017 | East et al. | |
| 9,782,536 | B2 | 10/2017 | Skutnik et al. | |
| 9,919,102 | B2 | 3/2018 | John | |
| 9,981,117 | B2 | 5/2018 | Brandt et al. | |
| 9,993,600 | B2 | 6/2018 | Lanier, Jr. et al. | |
| 10,238,851 | B2 | 3/2019 | Butziger et al. | |
| 10,376,635 | B2 | 8/2019 | Haase | |
| 10,589,024 | B2 | 3/2020 | John | |
| 10,596,362 | B2 | 3/2020 | Fielder et al. | |
| 10,625,060 | B2 | 4/2020 | Børgesen | |
| 2005/0124980 | A1 | 6/2005 | Sanders | |
| 2005/0137537 | A1 | 6/2005 | Watson et al. | |
| 2007/0106280 | A1 * | 5/2007 | Utard | A61M 5/14276 604/500 |
| 2007/0112291 | A1 | 5/2007 | Børgesen | |
| 2010/0030196 | A1 | 2/2010 | Hildebrand et al. | |
| 2016/0089521 | A1 | 3/2016 | Dragoon et al. | |
| 2017/0325685 | A1 | 11/2017 | Shachar et al. | |
| 2018/0117243 | A1 | 5/2018 | Maguire | |
| 2019/0009014 | A1 | 1/2019 | Chen et al. | |
| 2019/0184139 | A1 | 6/2019 | Nelson et al. | |
| 2019/0269850 | A1 | 9/2019 | Shih et al. | |
| 2020/0061362 | A1 | 2/2020 | Singh et al. | |

FOREIGN PATENT DOCUMENTS

| | | | |
|---|---|---|---|
| WO | WO2009129474 | A1 | 10/2009 |
| WO | WO2012138854 | A1 | 10/2012 |
| WO | WO2013134486 | A4 | 9/2013 |
| WO | WO2016059162 | A1 | 4/2016 |
| WO | WO2020046791 | A1 | 3/2020 |

OTHER PUBLICATIONS

Alcyone Lifesciences, Inc., Bringing Hope to Spinal Muscular Atrophy (SMA) Patients with the Alcyone Lifesciences ThecaFlex DRx™ System Breakthrough Device, Dec. 2, 2019, 3 pages, available at: https://www.prnewswire.com/news-releases/bringing-hope-to-spinal-muscular-atrophy-sma-patients-with-the-alcyone-lifesciences-thecaflex-drx-system-breakthrough-device-300967222.html.

* cited by examiner

IMPLANTABLE DRUG DELIVERY PORT

TECHNICAL FIELD

The present disclosure relates generally to implantable medical devices, and more particularly implantable drug delivery ports (also referred to as access ports) used to deliver pharmaceutical agents to target regions in the body.

BACKGROUND

A variety of medical devices are used for acute, chronic, or long-term delivery of therapy to patients suffering from a variety of conditions, such as chronic pain, tremor, Parkinson's disease, cancer, epilepsy, urinary or fecal incontinence, sexual dysfunction, obesity, spasticity, or gastroparesis. Drug access ports or other fluid delivery devices can be used for chronic delivery of pharmaceutical agents. Typically, such devices provide therapy by periodic injections aided by the port or other device to gain access to key positions within a patient's body such as the cerebrospinal fluid (CSF).

Implantable drug infusion ports can provide important advantages over other forms of medicament administration. For example, oral administration is often difficult because the systematic dose of the substance needed to achieve the therapeutic dose at the target site may be too large for the patient to tolerate without adverse side effects. Also, some substances simply cannot be absorbed in the stomach adequately for a therapeutic dose to reach the target site. Moreover, substances that are not lipid soluble may not cross the blood-brain barrier adequately if needed in the brain via oral administration. Implantable drug ports can help with these issues as well as help avoid the problem of patient noncompliance.

Implantable drug ports are typically implanted at a location within the body of a patient (typically a subcutaneous region in the lower abdomen) and are configured to deliver a fluid medicament through a catheter to a target treatment site. Drug ports typically receive percutaneous bolus injections via a syringe—the needle of the syringe is inserted through the skin of the patient, piercing a septum of the implantable drug port. The pharmaceutical agent is injected into the implantable drug port, which then delivers the pharmaceutical agent to the target treatment site via the catheter. The catheter used in these devices is generally configured as a flexible tube with a lumen running the length of the catheter that transports the pharmaceutical agent from the drug port to a target treatment site within the patient's body.

Further, conventional ports include multi-component constructions allowing for possibilities of system malfunction or reduced long-term reliability. For example, traditional catheter fitting designs are manufactured separate from the drug delivery system (e.g., drug port/port housing) and incorporated using a press fit and/or gasket seal. Such seals can degrade with time limiting the lifespan of the device and presenting a point for possible leakage.

The present disclosure may address one or more of these concerns.

SUMMARY

Embodiments of the present disclosure provide a system to provide drug delivery with improved efficiency in drug delivery and with improved patient fluid sampling capabilities. The disclosed implantable drug port includes a mechanical filter that includes a plurality of filter channels circumferentially aligned in a single plane about a fill port cavity. The mechanical filter allows for the capture of certain large particulate debris such as fragmented septum pieces to be captured and prevented from being introduced to the treatment site. Additionally, the relatively large cross-section of the filter channels compared to the mesh size of traditional bacterial retentive filters (e.g., on the order of about 0.2 μm) helps prevent clogging due to the passage of the pharmaceutical fluid through the filter channels. Further, the relatively large cross-section of the filter channels may allow for the convenient collection of sample fluid (e.g., CSF fluid) from the drug delivery port.

In an embodiment, the disclosure describes an implantable drug delivery port including a port housing having an inner sidewall and a needle stop that define a fill port cavity for receiving an injectable fluid and a catheter fitting configured to couple to a catheter, where the inner sidewall includes a perimeter edge and the catheter fitting defines an inner lumen in fluid communication with the fill port cavity. The implantable drug delivery port also includes a fill port washer having a first side and a second side opposite the first side where the first side is in direct contact with the perimeter edge of the inner sidewall of the port housing. An intersection between the first side of the fill port washer and the perimeter edge of the inner sidewall define a plurality of filter channels where each filter channel has a cross-sectional flow area of about 0.001 $mm^2$ to about 0.5 $mm^2$ and lies within a fluid pathway between the fill port cavity and the inner lumen of the catheter fitting. The implantable drug delivery port also includes a pierceable septum in direct contact with the second side of the fill port washer and a port cover coupled to the port housing so that the pierceable septum is compressed between at least the second side of the fill port washer and the port cover, where the port cover defines an aperture positioned over the pierceable septum, and the drug delivery port is configured to allow a needle to pierce through the septum to deliver the injectable fluid to the fill port cavity.

In another embodiment, the disclosure describes a drug delivery system comprising the disclosed drug delivery port and a catheter having a proximal end configured to be coupled to the catheter fitting of the drug delivery port.

In another embodiment, the disclosure a method of forming an implantable drug delivery port having a port housing, a fill port washer, a pierceable septum, and a port cover. The method includes machining the port housing to include an inner sidewall and needle stop defining a fill port cavity for receiving an injectable fluid, where the inner sidewall includes a perimeter edge. The method also includes machining at least one of the perimeter edge of the inner sidewall or a first side of the port washer to form a plurality of filter channels, wherein each filter channel defines a cross-sectional flow area of about 0.001 $mm^2$ to about 0.5 $mm^2$ when the first side of the port washer is seated in direct contact with the perimeter edge of the inner sidewall, and coupling the port cover to the port housing so that the pierceable septum is compressed between at least a second side of the fill port washer and the port cover, where the port cover defines an aperture positioned over the pierceable septum and configured so that a needle can pierce through the septum to deliver the injectable fluid to the fill port cavity.

Further, embodiments of the disclosed implantable drug port include an integrated catheter fitting. The integrated catheter fitting allows for a one-piece construction between the port housing and catheter fitting thereby eliminating the potential of leaks around the catheter fitting to occur and creating a more robust and reliable system.

The above summary is not intended to describe each illustrated embodiment or every implementation of the subject matter hereof. The figures and the detailed description that follow more particularly exemplify various embodiments.

BRIEF DESCRIPTION OF DRAWINGS

The disclosure can be more completely understood in consideration of the following detailed description of various embodiments of the disclosure, in connection with the accompanying drawings, in which.

Figure 1:
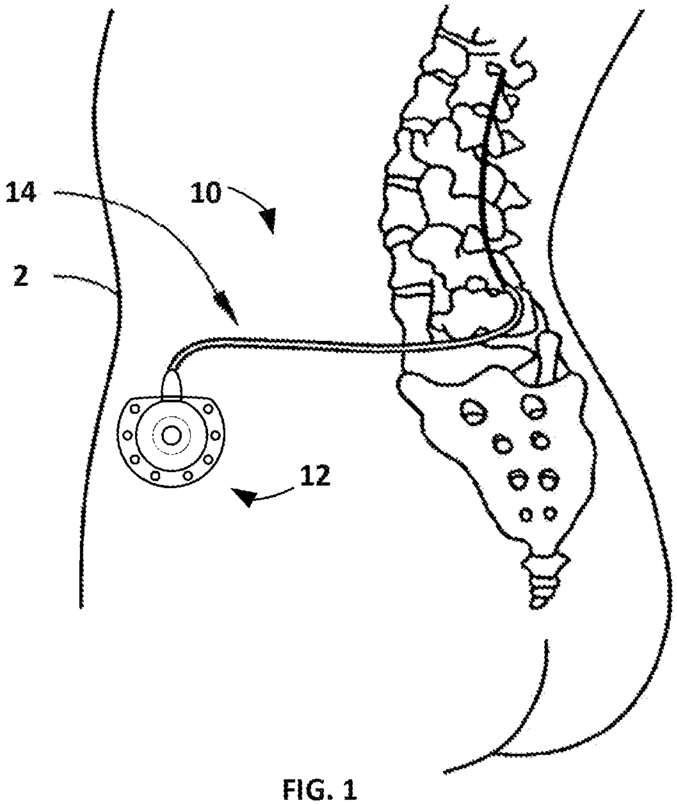
FIG. 1 is a schematic diagram of a portion of an implantable drug delivery system that includes a drug delivery port implanted within the body of a patient.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

FIG. 1 is a schematic diagram showing an implanted drug delivery system 10 for introducing pharmaceutical agents to target treatment sites within the body of a patient 2. FIG. 1 shows the lower abdomen of patient 2 and drug delivery system 10, which includes drug delivery port 12 and catheter 14 implanted in patient 2. Drug delivery port 12 may alternately be referred to as an access port. Although depicted in connection with a human body, it should be understood that drug delivery system 10 of the present invention could also be used on non-human animals.

Drug delivery port 12 may be used for infusing a fluid containing one or more pharmaceutical agents into the various target locations of patient 2 such as the CSF within the spinal canal, deep brain structures, or other desired locations. Access ports mounted within the abdomen of a patient may be advantageous to deliver pharmaceutical agents directly to CSF within the spinal canal of a patient. This approach offers a less invasive alternative that relies on the indirect delivery of the pharmaceutical agent to the brain by delivering the agent to the CSF and relying on diffusion of the pharmaceutical agent within the CSF to reach the brain.

Drug delivery port 12 is configured to be implanted within patient 2 and receive a therapeutic fluid containing one or more pharmaceutical agents via a percutaneous bolus injection. The therapeutic fluid is then transported through catheter 14 to the target treatment site such as the CSF within patient 2. Drug delivery port 12 may be surgically implanted subcutaneously in the pectoral, abdominal, lower back region, or other desirable location within patient 2.

Figure 2:
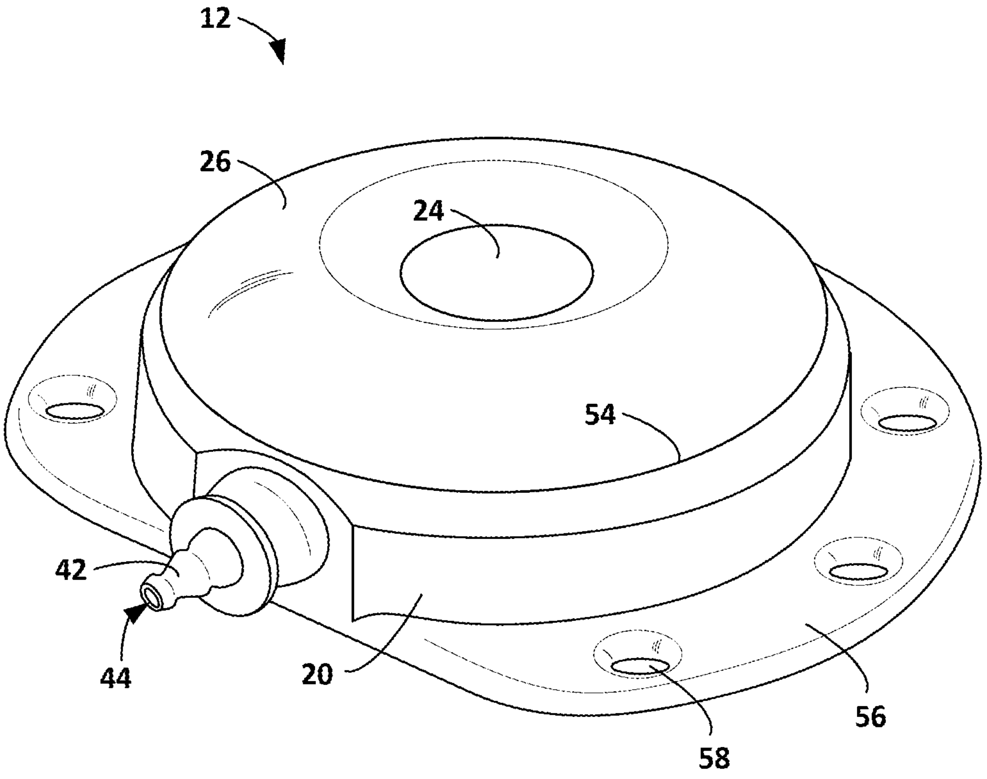
FIG. 2 is a schematic perspective view of the drug delivery port from FIG. 1.
Figure 3:
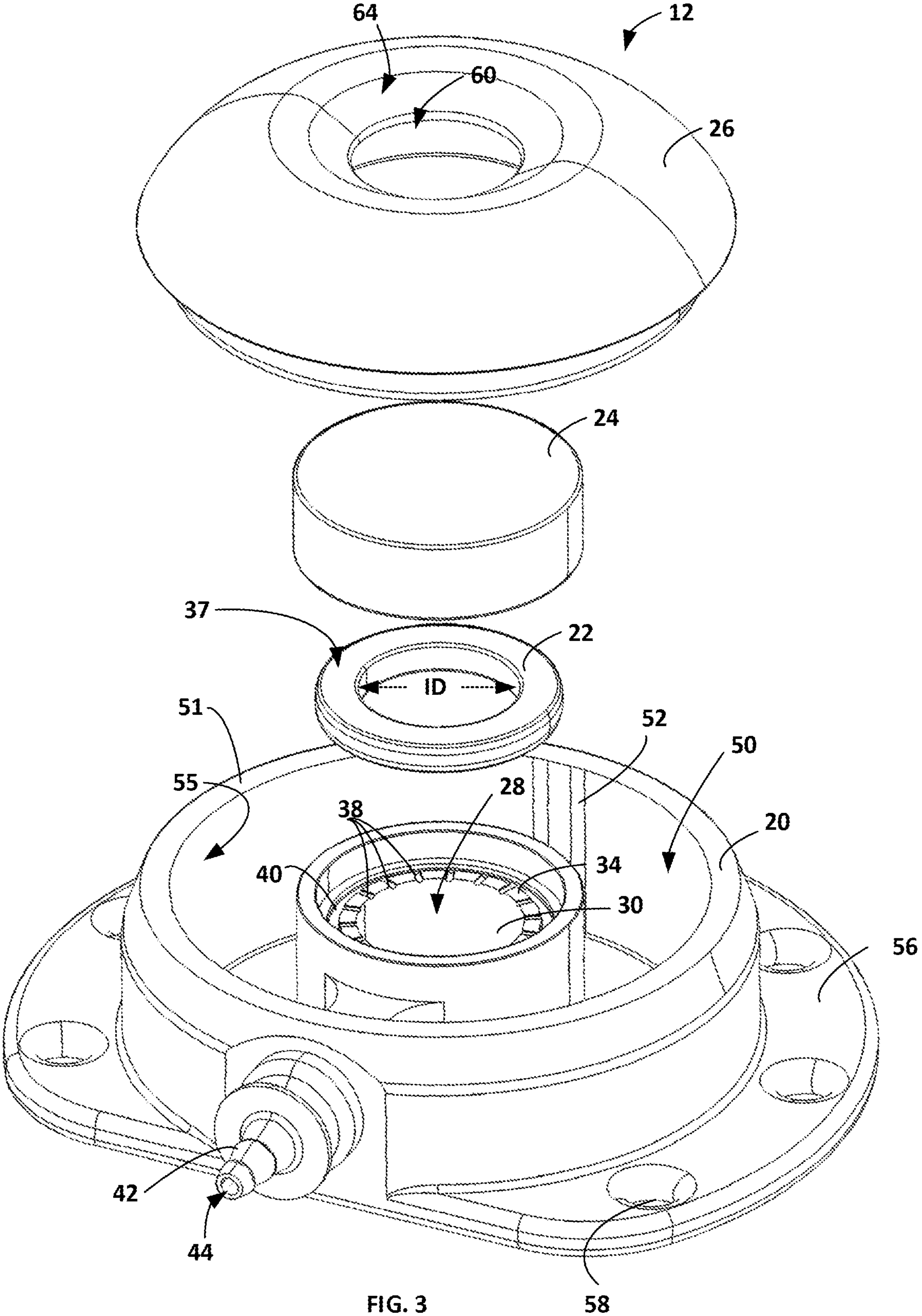
FIG. 3 is an exploded view of the drug delivery port from FIG. 2.
Figure 4:
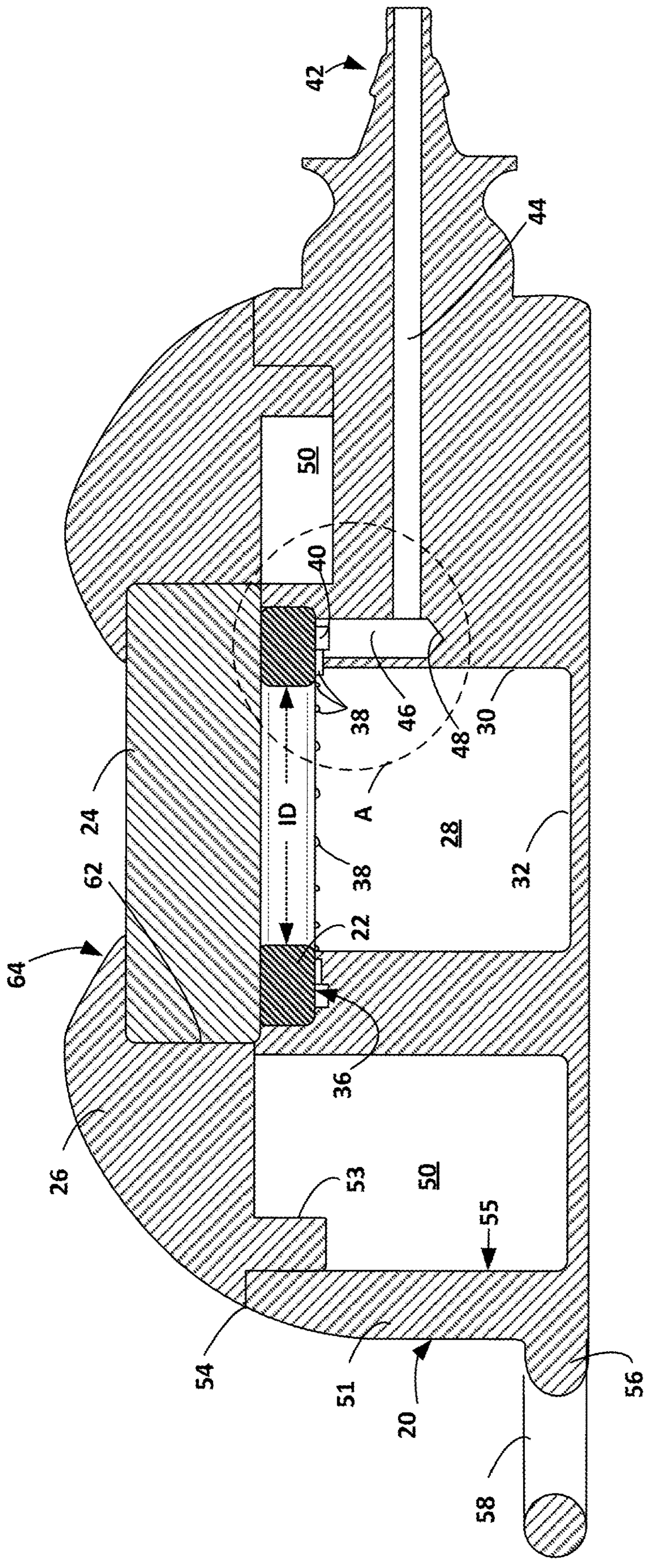
FIG. 4 is a cross-sectional view of the drug delivery port from FIG. 2.
Figure 5:
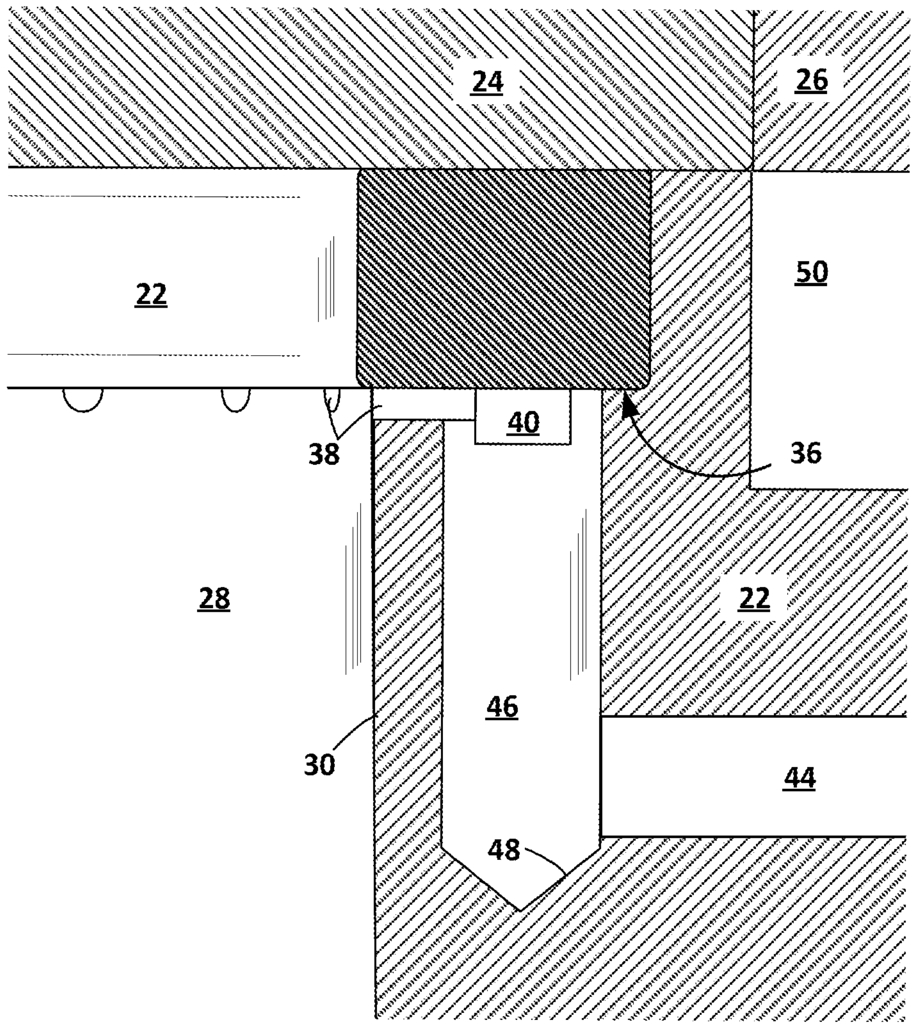
FIG. 5 is a close-up view of area A from FIG. 4.

As shown in FIGS. 2-4, drug delivery port 12 includes four primary components including a port housing 20, fill port washer 22, fill port septum 24, and port cover 26. As discussed in further detail below, the interior of port housing 20 defines a fill port cavity 28 that is positioned near the center of port housing 20 and configured for receiving a bolus injection of a therapeutic fluid. In an assembled state, fill port washer 22 seats on an upper part of fill port cavity 28 (defined by port housing 20) such as a perimeter edge 34, followed by septum 24 positioned atop of fill port washer 22 such that the interior ring of fill port washer 22, an interior surface of septum 24, and fill port cavity 28 collectively form the reservoir volume of drug port 12 that receives the injected therapeutic fluid.

Referring first to port housing 20, in some examples, fill port cavity 28 may be constructed as a cylindrical chamber that is defined by an inner sidewall 30 and needle stop 32 of port housing 20. Needle stop 32 forms a lower surface of fill port cavity 28 (e.g., the surface opposite of septum 24) and acts as a stop barrier for a needle introduced into fill port cavity 28 through septum 24. While needle stop 32 is generally shown as being a circular, flat surface, in other examples the surface of needle stop 32 may take on a different shape or design including, for example, domed or conical. The upper portion of sidewall 30 terminates in perimeter edge 34 which is brought into direct contact against a first side 36 of fill port washer 22.

A plurality of filter channels 38 are defined along the intersection between fill port washer 22 and perimeter edge 34. Filter channels 38 lie within the fluid pathway through drug delivery port 12 and form the exit path for fluid introduced into fill port cavity 28. Filter channels 38 act as a mechanical filter within drug delivery port 12 and are each sized to prevent larger debris such as septum coring or tear outs (e.g., produced by the introduction of a needle through septum 24) from exiting fill port cavity 28 or being passed through the device to the target treatment site.

Simultaneously, filter channels 38 are sufficiently sized so as not to impede or produce an occlusion of the flow of therapeutic fluid through drug delivery port 12, or likewise the sampling fluid (e.g., sampled CSF) passing through filter channels 38. As depicted generally in the Figures, filter channels 38 may comprise semi-circular channels. Alternately, filter channels 38 may comprise a U-shape, rectangular, square, V-shaped, circular bore, or other suitable configuration. For example, conventional filters in drug delivery pumps and other devices are commonly formed from a porous material or other small apertures/pore size materials on the order of about 0.2 μm. Such filters are designed to filter out biological materials or agglomerate material within the therapeutic fluid. However, such filter materials can become occluded overtime. Further, due to the function of such small pore size filters, sampling of fluid material (e.g., CSF) may not be possible as the filter acts to remove bio markers from the sampled fluid. Filter channels 38 are configured to sufficiently filter large debris materials such as cored septum particles, while simultaneously avoiding the drawbacks of a conventional filter.

Filter channels 38 may represent the narrowest cross section along the fluid flow pathway (e.g., cross-section flow area) through drug delivery port 12. Filter channels 38 may be similarly sized and extend radially outward from the central axis of fill port cavity 28. In some embodiments, each debris channel 38 may define cross-sectional flow area (e.g., area perpendicular to the flow direction) of greater than about 0.001 mm$^2$, greater than about 0.01 mm$^2$, greater than about 0.02 mm$^2$, or greater than about 0.025 mm$^2$. Likewise, each debris channel 38 may define cross-sectional area smaller than the smallest needle cross-section intended to be used to inject or sample fluid from fill port cavity 28 (e.g., 27 to 14 gauge needles have typical diameters between about 0.4 mm to about 1.8 mm). In some embodiments, each debris channel 38 may define cross-sectional flow area of less than about 0.5 mm$^2$, less than about 0.2 mm$^2$, or less than about 0.1 mm$^2$. In some example, each debris channel 38 may define a cross-section that is semi-circular (e.g., half circle) with dimensions of approximately 0.010 inches wide by 0.005 inches deep.

Any suitable number of filter channels 38 may be incorporated into drug delivery port 12 but should be enough to not unnecessarily increase the flow resistance through port 12. In some embodiments, drug delivery port 12 may include about 2 to about 25, or about 5 to about 20 total filter channels 38.

Filter channels 38 may be defined by the contact intersection between first side 36 of fill port washer 22 and perimeter edge 34 of sidewall 30 such that filter channels 38 are circumferentially aligned within a common plane such as defined by perimeter edge 34. In some embodiments, filter channels 38 may be defined by the perimeter edge 34 of sidewall 30. Such a construction allows for the convenient machining of filter channels 38 during the construction of port housing 20. For example, after the formation of fill port cavity 28, each filter channel 38 may be machined (e.g., CNC machined or laser cut) into inner sidewall 30 of port housing 20 along perimeter edge 34. In other embodiments, filter channels 38 may be formed along first surface 36 of fill port washer 22 or a combination of first side 36 of fill port washer 22 and perimeter edge 34.

Continuing along the fluid pathway through drug delivery port 12, each filter channel 38 directly fluidically connects to collection channel 40. Collection channel 40 may be in the form of a ring-shaped channel aligned coaxially (e.g., shares a common central axis) with fill port cavity 28. Fluid introduced intro fill port cavity 28 will directly pass through filter channels 38 where the fluid is then recollected in collection channel 40. The cross-section of collection channel 40 may be larger than the cross-section of a single filter channel 38. Similar, to filter channels 38, the surrounding walls that define collection channel 40 may be formed by both part of port housing 20 and fill port washer 22. Further, like filter channels 38, collection channel 40 may be continently machined into port housing 20 during the manufacturing process.

After entry into collection channel 40, the injected fluid passes through one or more lumens defined within port housing 20 until the fluid exits through catheter fitting 42 and enters catheter 14.

In some embodiments, catheter fitting 42 may be manufactured separate from port housing 20 and connected during assembly. Such an assembly however introduces additional components into the design of drug delivery port 12 which can create additional points for possible failure or reduced reliability within the system.

Referring now to catheter fitting 42, to improve upon drawbacks of prior configurations, catheter fitting 42 may be integrally formed with port housing 20 such that catheter fitting 42 is completely integrated with port housing 20. Catheter fitting 42 is thus formed from the same structure as port housing 20 such that catheter fitting 42 is a portion of, and inseparable from, port housing 20. The integrated catheter fitting 42 design eliminates the need for a seal between the stem and port housing as the two components are manufactured using a single piece of material. Catheter fitting 42 may be machined to include a fir-tree, barb, flare, lip or other suitable style connector assembly for receiving and coupling to a proximal end of catheter 14 during system implantation.

The integrated design of catheter fitting 42 can substantially improve the robustness and reliability of drug delivery port 12 and increase the intended life span for the device. For example, the entire drug delivery port 12 may be constructed using only four distinct components, e.g., port housing 20, fill port washer 22, fill port septum 24, and port cover 26, thereby reducing the number of seams and seals within the system and the chance of component failure compared to traditional devices.

With the integrated catheter fitting 42 design, the fluid exit pathway through port housing 20 is machined directly into port housing 20. In some embodiments, the fluid pathway between collecting channel 40 and the outlet of catheter fitting 42 may be produced by the creation of a first lumen 44 horizontally machined along a central axis of catheter fitting 42 and a second lumen 46 machined into port housing 20 that directly fluidically connects collecting channel 40 and first lumen 44. The volume of first and second lumens 44 and 46 may be relatively small so as to maintain a relatively low fluid volume within drug delivery port 12.

Each of first and second lumens 44 and 46 may be produced using any suitable technique. In some embodiments, the lumens may be formed using a combination of mechanical drilling and electrical discharge machining (EDM). For example, first lumen 44 may be machined first using mechanical drilling laterally through catheter fitting 42 into port housing 20, toward fill port cavity 28. The lumen 44 may be cut through the port housing 20 a set distance so as to provide intersection with second lumen 46 once second lumen 46 is formed. As first lumen 44 is machined first, the leading edge of first lumen 44 is not of great significance because the leading edge of first lumen 44 will be removed by the formation of second lumen 46.

The formation of second lumen 46 may be formed after the creation of first lumen 44. However, because second lumen 46 represents a blind cut rather than a through cut, the leading edge 48 of second lumen 46 is of more consequence than that of first lumen 46. It was found that if second lumen 46 were mechanically drilled into port housing 20, leading edge 48 and the intersection with first lumen 44 had the potential of creating micro burs along the intersection. Such burs would need to be removed prior to assembly of drug delivery port 12 to eliminate the risk of introducing such burs into the target treatment site. Conventionally, implantable drug delivery devices included bacterial retentive filters that would inherently collect such debris prior to fluid entry into catheter 14. However, such bacterial retentive filters included in drug delivery port 12 would negatively impact the sampling capabilities of the port as described above. It was found that by forming second lumen 46 using EDM as opposed to mechanical drilling, the presence of such burs was eliminated creating a clean connection between first and second lumens 44 and 46 that did not require further processing.

The above construction allows for the fluid volume defined by filter channels 38, collecting channel 40, and lumens 44 and 46 to remain relatively small. Having the internal volume of such internal passageways remain relatively small helps reduce the amount of flush fluid needed to be injected after the delivery of the therapeutic fluid to ensure complete delivery of the therapeutic fluid to the target treatment site at the distal end of catheter 14. In some embodiments, the fluid volume occupied by filter channels 38, collecting channel 40, lumens 44 and fill port cavity 28) may be about 0.20 mL to about 0.35 mL. In a dry, assembled state (e.g., not including a therapeutic fluid), drug delivery port 12 may weigh between about 10 grams and about 20 grams (e.g., about 17 grams) to provide suitable patient comfort across multiple age groups. In an example, drug delivery port 20 may weigh less than approximately twenty grams when empty. Additionally, drug delivery port 12, may define a total external volume (e.g., including the volumes defined by fill port cavity 28, void chamber 50, and the like) of about 4 cubic centimeters (cc) to about 8 cc, or about 5.5. cc to about 6.5.

As shown in FIGS. 3 and 4, port housing 20 may also define one or more void chambers 50 within the interior space of port housing 20. Void chamber 50 represents empty space within the interior of drug delivery port 12 and is fluidically isolated from fill port cavity 28 when drug delivery port 12 is assembled, nor does void chamber 50 play a role with the drug delivery process. Instead, void chamber 50 acts as a negative space to increase the overall size and volume of drug delivery port 12 without contributing to the overall weight of port 12. In some embodiments, void chamber 50 may be in the form of a semi cylindrical or horseshoe shape chamber coaxially aligned with fill port cavity 28, although other shapes and designs are also envisioned.

Void chamber 50 may be defined in part by exterior sidewall 51 of port housing 20 which contacts and is secured to port cover 26 upon assembly. Either exterior sidewall 51 or port cover 26 may include one or more alignment features (e.g., raised lip 53) that contributes to the proper alignment and seating of port cover 26 to port housing 20. In some examples, an interior surface 55 of exterior sidewall 51 may include one or more press-fit retainers 52 (e.g., a small protrusion) configured to produce a friction fit with port cover 26 when the two components are press fit together. Interior surface 55 may include one or more retainers 52 at one or more locations—for example, pairs of retainers 52 distributed at multiple locations around interior surface 55. In addition or alternatively, lip 53 of port cover 26 may include similar retainer features. In embodiments, retainers 52 may protrude approximately 0.0005 to about 0.05 inches as desired.

The retainers 52 provide temporary securement between port housing 20 and port cover 26 during the manufacturing process until port housing 20 and port cover 26 can be welded together along seam 54, by creating a tight press-fit between port housing 20 and port cover 26. The inclusion of retainers 52 thus eliminates the need to fixture the two components together, tack weld the two components, remove fixture, and then perform final seam weld of the port assembly, thereby improving the ease of manufacturing.

The overall shape of port housing 20 may be cylindrical with the catheter fitting 42 protruding radially outward from one side. In some embodiments, port housing 20 may also include a suture flange or skirt 56 containing one or more suture points 58 therein. Suture flange 56 may extend radially outward from the base of port housing 20 (e.g., side opposite where port cover 26 attaches) and may partially encircle port housing 20 so as to not interfere with the securement of catheter 14 to catheter fitting 42. Suture flange 56 may be integrally formed with port housing 20.

Port housing 20 may be composed of any suitable material including, for example, constructed of a material that is biocompatible such as titanium, tantalum, stainless steel, plastic, ceramic, or the like. In some embodiments, port housing 20 may be constructed from a single piece of titanium (e.g., grade 2 titanium). Titanium offers the advantages of being inert to both the patient as well as most pharmaceutical agents and solutions.

Referring now to other components of drug delivery port 12, as discussed above drug delivery port 12 also includes fill port washer 22 configured to seat within the interior space of port housing 20 in direct contact with perimeter edge 34. Fill port washer 22 is composed of a non-compressible material (e.g., titanium or similar material as port housing 20) such that when drug delivery port 12 is assembled and septum 24 is compressed between at least port cover 26 and fill port washer 22 and optionally port housing 20, the intersection between first side 36 of fill port washer 22 and edge perimeter 38 does not deform, thereby maintaining the establishment of filter channels 38 and collection channel 40.

In some embodiments, the inner diameter (ID) of fill port washer 22 may be sized slightly smaller than the diameter of fill port cavity 28. Such a configuration may help prevent the possibility of a needle catching on one of filter channels 38 or perimeter edge 34. Similarly, the diameter of aperture 60 within port cover 22, may be slightly smaller than ID of fill port washer 22 to reduce the likelihood of the needle catching on the intersection between septum 24 and fill port washer 22. Additionally, or alternatively, one or more of the edges of fill port washer 22 or perimeter edge 34 may be rounded to help redirect any glances from a needle into fill port cavity 28. In some embodiments, the ID of fill port washer 22 may be about 3 mm to about 10 mm, about 5 mm to about 8 mm, or about 6 mm to about 7 mm, however other diameters are also envisioned.

Drug delivery port 12 also includes fill port septum 24. Fill Port Septum 24 may be comprised of a self-sealing, pierceable material that enables a needle to access fill port cavity 28 percutaneously. Suitable materials may include, but are not limited to, silicone. Unlike fill port washer 22, fill port septum 24 may be compressible or deformable to ensure a seal between fill port septum 24 and port cover 26.

Fill Port Septum 24 forms a seal against aperture 60 of port cover 26. In some embodiments, the interior surface of port cover 26 may include an interior retaining cup 62 configured to receive septum 24 during assembly of drug delivery port 22. Retaining cup 62 may include a cylindrical ring that receives and retains septum 24 via a press fit. Upon full assembly of drug delivery port 12, septum will be compressed between port cover 26 and fill port washer 22 and port housing 20. The inclusion of retaining cup 62 within port cover 26 may help compress septum 24 to force the septum against the perimeter edge of aperture 60 to provide a secure seal there between.

Port cover 26 may be constructed of the same material as port housing 20 (e.g., titanium). Further, port cover 26 may have a partial torus shape such that it forms a smooth, convex contour with exterior wall 51 of port housing 20 along seam 54 while also helping to provide a funneling surface 64 toward aperture 60 and fill port septum 24. Funneling surface 64 may assist with allowing the clinician to palpitate the location of fill port septum 24 as well as help direct the tip of a needle toward aperture 60.

The exterior surfaces of drug delivery port 12 intended to be placed in direct contact with the patient may be smooth and rounded so as not to include any abrupt corners that may cause irritation to the patient.

Drug delivery system 10 also includes catheter 14 having an elongated tubular portion that extends from the proximal end coupled to catheter fitting 42 to a distal end and defines an inner catheter lumen. Drug delivered from drug delivery port 12 passes through the lumen of catheter 14 and exits the catheter through one or more openings at or near the distal end implanted at a target treatment site. When implanted for delivering drugs to the spinal region, at least a portion of catheter 14 is located intrathecally within the CSF of the patient such that as drug exits catheter 14 and enters directly into the CSF such that the pharmaceutical agent does not contact other tissues or bodily fluids before reaching the CSF of the patient.

The body of catheter 14 may be constructed using any suitable material, e.g., an elastomeric tube. When implanted in the spinal canal, catheter 14 may be floating free in the CSF and may contact the spinal cord of the patient. As a result, catheter 14 may preferably be soft and flexible to limit any chance of damaging the spinal cord. Examples of some suitable materials include, but are not limited to, silicone rubber (e.g., polydimethyl siloxane) or polyurethane, both of which can provide good mechanical properties and are very flexible. Suitable materials for catheter 14 are also preferably chemically inert such that they will not interact with drugs or body tissue or body fluids over a long time period.

The inside diameter of catheter 14 is preferably large enough to accommodate expected infusion rates with acceptable flow resistance for delivery of the pharmaceutical agent to a target treatment site as known by those in the art. As an example, catheter 14 may have an outside diameter of about 1.2 mm to about 2.0 mm and an inside diameter of about 0.4 mm to about 0.6 mm. In some embodiments, catheter 14 may be about 5 centimeters (cm) to about 150 cm long to reach from, e.g., drug port 12 implanted in the patient's abdomen to the spine. In some embodiments, catheter 14 may include one or more segments, connectors, or other components.

The disclosed drug delivery system 10 may be used to treat various neurological diseases; examples are chronic pain, chronic pain, tremors, Parkinson's disease, cancer, epilepsy, urinary or fecal incontinence, sexual dysfunction, obesity, spasticity, gastroparesis, or other disorders. Various types of pharmaceutical agents may be used for the treatment of such diseases. Examples of possible pharmaceutical agents that can be used with system 10 include, but is not limited to, one or more of Gabapentin, Baclofen, Midazolam, or Valproate Na for the treatment of epilepsy; insulin for the treatment of diabetes, analgesics for pain management; disease modifying drugs for CNS disorders; and the like. For effective delivery, the distal end of catheter 14 may be positioned within the CSF, portions of the brain, other locations, or combinations thereof.

Figure 6:
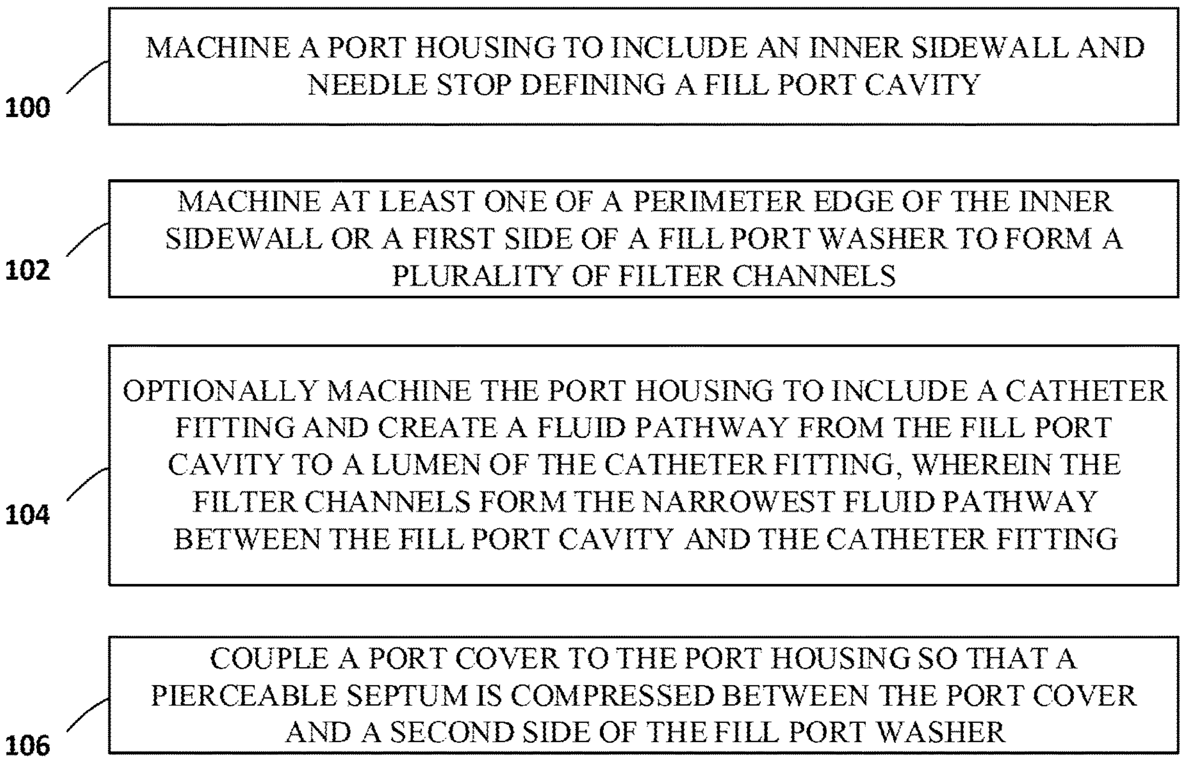
FIG. 6 is a flow diagram of a method of producing the drug delivery port of FIG. 2.

FIG. 6 is a flow diagram of a method of manufacturing or producing drug delivery port 12. The method depicted in FIG. 6 includes machining a port housing 12 to include an inner sidewall 30 and needle stop 32 that define a fill port cavity 28 (100), machining at least one of perimeter edge 34 of inner sidewall 30 or a first side of fill port washer 22 to include a plurality of filter channels 38 (102), optionally machine the port housing to include a catheter fitting 42 and creating a fluid pathway (e.g., collecting channel 40, first lumen 44, and second lumen 46) from fill port cavity 28 to first lumen 44 of catheter fitting 42 (104), and coupling a port cover 26 to port housing 20 so that a pierceable septum 24 is compressed between at least port cover 26 and a second side 37 of fill port washer 22 (106).

As discussed above, the fluid pathway between filter channels 38 and catheter fitting 42 may be formed using a combination of mechanical machining and EDM. More specifically, first lumen 44 and collecting channel 40 may be mechanically machined (e.g., CNC or drilled) followed by EDM to form second lumen 46 directly fluidically connecting collecting channel 40 and first lumen 44.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A method of forming an implantable drug delivery port comprising a port housing, a fill port washer, a pierceable septum, and a port cover, the method comprising:

machining the port housing to include an inner sidewall and needle stop defining a fill port cavity for receiving an injectable fluid, wherein the inner sidewall comprises a perimeter edge;

machining at least one of the perimeter edge of the inner sidewall or a first side of the port washer to form a plurality of filter channels, wherein each filter channel defines a cross-sectional flow area when the first side of the port washer is seated in direct contact with the perimeter edge of the inner sidewall; and coupling the port cover to the port housing so that the pierceable septum is compressed between at least a second side of the fill port washer and the port cover, wherein the port cover defines an aperture positioned over the pierceable septum and is configured so that a needle can pierce through the septum to deliver the injectable fluid to the fill port cavity.

2. The method of claim 1, further comprising:

machining the port housing to include an integrated catheter fitting; and machining the port housing to form a fluid pathway that connects the plurality of filter channels to the catheter fitting.

3. The method of claim 2, wherein machining the port housing to form a fluid pathway comprises:

forming a collecting channel coaxially aligned with the fill port cavity and fluidically connected to each of the plurality of filter channels;

machining a first lumen along a central axis of the catheter fitting; and electrical discharge machining a second lumen to fluidically connect the collecting channel to the first lumen.

4. The method of claim 1, wherein coupling the port cover to the port housing comprises:

press fitting the port cover to the port housing, wherein at least one of the port cover or the port housing comprises at least one friction-fit retainer that temporarily secures the port housing to the port cover; and welding the port housing to the port cover.

* * * * *